(12) United States Patent
Li et al.

(10) Patent No.: US 9,554,727 B2
(45) Date of Patent: Jan. 31, 2017

(54) ATHEROSCLEROSIS CHARACTERIZATION USING A MULTI-CONTRAST MRI SEQUENCE

(71) Applicant: Cedars-Sinai Medical Center, Los Angeles, CA (US)

(72) Inventors: Debiao Li, South Pasadena, CA (US); Zhaoyang Fan, Irvine, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 701 days.

(21) Appl. No.: 13/970,327

(22) Filed: Aug. 19, 2013

(65) Prior Publication Data

US 2015/0048821 A1 Feb. 19, 2015

(51) Int. Cl.
*G01R 33/56* (2006.01)
*A61B 5/055* (2006.01)
*A61B 5/02* (2006.01)
*G01R 33/563* (2006.01)

(52) U.S. Cl.
CPC ........... *A61B 5/055* (2013.01); *A61B 5/02007* (2013.01); *G01R 33/5602* (2013.01); *G01R 33/5607* (2013.01); *G01R 33/5635* (2013.01)

(58) Field of Classification Search
CPC . A61B 5/055; A61B 5/02007; G01R 33/5602; G01R 33/5607; G01R 33/5635
See application file for complete search history.

(56) References Cited

U.S. PATENT DOCUMENTS

| | | | | |
|---|---|---|---|---|
| 6,397,096 B1 * | 5/2002 | Liu | ...................... | G01R 33/563 324/307 |
| 7,283,862 B1 * | 10/2007 | Slavin | ................ | G01R 33/4835 324/306 |
| 2014/0296700 A1 * | 10/2014 | Gulani | ............... | G01R 33/3614 600/414 |

OTHER PUBLICATIONS

Xie et al. 3D coronary dark-blood interleaved with gray-blood (cDIG) MRI [Online] Jan. 16, 2014, Journal of Cardiovascular Magnetic Resonance, 16(Suppl 1):P217, [Retrieved from the Internet] <http://jcmr-online.biomedcentral.com/articles/10.1186/1532-429X-16-S1-P217>.*
Nayak KS, Hu BS. The future of real-time cardiac magnetic resonance imaging. Curr Cardiol Rep 2005;7:45-51.
Yuan C et al. Circulation 2001;104:2051.

* cited by examiner

*Primary Examiner* — David Gray
*Assistant Examiner* — Laura Roth
(74) *Attorney, Agent, or Firm* — Nixon Peabody LLP; Linda B. Huber

(57) ABSTRACT

The present invention relates to imaging and characterizing atherosclerotic lesions. The invention utilizes a low-flip-angle gradient echo-based MRI acquisition technique combined with specialized magnetization preparative schemes (i.e. non-selective inversion and FSD), and multiple co-registered 3D image sets with different contrast weightings are collected in an interleaved fashion. Using the inventive method, a single scan allows for comprehensive assessment of atherosclerotic plaque within just a few minutes.

17 Claims, 5 Drawing Sheets

ATHEROSCLEROSIS CHARACTERIZATION USING A MULTI-CONTRAST MRI SEQUENCE

FIELD OF THE INVENTION

The present invention generally relates to imaging methods, and more specifically those used for detecting and analyzing atherosclerosis.

BACKGROUND

The following description includes information that may be useful in understanding the present invention. It is not an admission that any of the information provided herein is prior art or relevant to the presently claimed invention.

The conventional MRI protocol for investigating atherosclerotic plaques involves a series of scans that provide multiple contrast weightings (e.g. T1-weighted, T2-weighted, and bright-blood, etc.) for resolving high-risk plaque characteristics. Unfortunately, misregistration between image sets due to inter-scan motion often compromises evaluation accuracy.

Considering the state of the art, there is clearly a need for improved MRI methods that allow for more efficient and accurate assessment of atherosclerotic plaque.

SUMMARY OF THE INVENTION

In various embodiments, the invention teaches a method for imaging an atherosclerotic lesion in a subject, including using an MRI machine to acquire multiple spatially co-registered 3D image sets in an interleaved fashion and from the same imaged volume of the subject, during a single scan. In some embodiments, the multiple spatially co-registered 3D image sets acquired provide multiple contrasts, including two or more of (1) black-blood hyper T1-weighting (T1-w), (2) grey-blood, and (3) black-blood T2-weighting (T2-w). In some embodiments, segmental sampling is periodically conducted following a non-selective inversion magnetization preparation. In certain embodiments, imaging is accomplished by performing steps, including: (1) applying a non-selective inversion pulse to a volume of interest (VOI) in the subject; (2) applying a first flow-sensitive dephasing (FSD) preparation; (3) acquiring hyper T1-weighted data from the VOI in the subject; (4) acquiring grey-blood data from the VOI in the subject, subsequent to and dependent upon blood signal recovery and the inflow of fresh blood in a vessel within the VOI; (5) applying a second FSD preparation; and (6) acquiring T2-weighted data from the VOI at the end of the inversion recovery. In some embodiments, the duration of the first FSD preparation is shorter than that of the second FSD preparation. In various embodiments, the subject scanned is a mammal. In some embodiments, the subject scanned is a human. In certain embodiments, the VOI includes a region of the subject's heart. In various embodiments, the VOI includes one or more anatomical structures selected from the group consisting of: an arterial wall, the brain, heart muscle, and parenchyma of an organ.

In various embodiments, the invention teaches a method for characterizing one or more atherosclerotic lesions in a subject. In some embodiments, the method includes (a) viewing images of the subject obtained by performing a method described herein; and (b) characterizing one or more atherosclerotic lesions in the subject on the basis of the presence or absence and/or extent of one or more characteristics demonstrated in the images and selected from the group consisting of: (i) intra-plaque hemorrhage, (ii) calcified nodules, (iii) dense fibrous material, (iv) necrotic core, and (v) loose matrix. In some embodiments, the one or more atherosclerotic lesions are further characterized by determining whether any hemorrhage detected is relatively new or relatively old, based upon one or more of the images viewed. In certain embodiments, any hemorrhage detected is characterized as relatively new or relatively old, based upon its signal appearance relative to other surrounding tissues on the T2-weighted image set.

In various embodiments, the invention teaches a magnetic resonance imaging system, including: a magnet operable to provide a magnetic field; a transmitter operable to transmit to a region within the magnetic field; a receiver operable to receive a magnetic resonance signal from the region; and a processor operable to control the transmitter and the receiver; wherein the processor is configured to direct the transmitter and receiver to execute a sequence, including (a) applying a non-selective inversion pulse to a volume of interest (VOI) in a subject; (b) applying a first flow-sensitive dephasing (FSD) preparation; (c) acquiring hyper T1-weighted magnetic resonance data from the VOI in the subject; (d) acquiring grey-blood magnetic resonance data from the VOI in the subject, subsequent to and dependent upon blood signal recovery and the inflow of fresh blood in a vessel within the VOI; (e) applying a second FSD preparation; and (f) acquiring T2-weighted data from the VOI at the end of the inversion recovery. In some embodiments, the processor is configured to generate an image based on the magnetic resonance data. In certain embodiments, the duration of the first FSD preparation is shorter than that of the second FSD preparation. In certain embodiments, the VOI includes a region of the subject's heart. In various embodiments, the VOI includes one or more anatomical structures selected from the group consisting of: an arterial wall, the brain, heart muscle, and parenchyma of an organ.

In various embodiments, the invention teaches a non-transitory machine-readable medium having machine executable instructions for causing one or more processors of a magnetic resonance imaging machine to execute a method, including: (a) applying a non-selective inversion pulse to a volume of interest (VOI) in a subject; (b) applying a first flow-sensitive dephasing (FSD) preparation; (c) acquiring hyper T1-weighted magnetic resonance data from the VOI in the subject; (d) acquiring grey-blood magnetic resonance data from the VOI in the subject, subsequent to and dependent upon blood signal recovery and the inflow of fresh blood in a vessel within the VOI; (e) applying a second FSD preparation; (f) acquiring T2-weighted magnetic resonance data from the VOI at the end of the inversion recovery; and (g) generating an image based on the magnetic resonance data. In certain embodiments, the duration of the first FSD preparation is shorter than that of the second FSD preparation. In various embodiments, the VOI includes a region of the subject's heart. In certain embodiments, the VOI includes one or more anatomical structures selected from the group consisting of: an arterial wall, the brain, heart muscle, and parenchyma of an organ.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
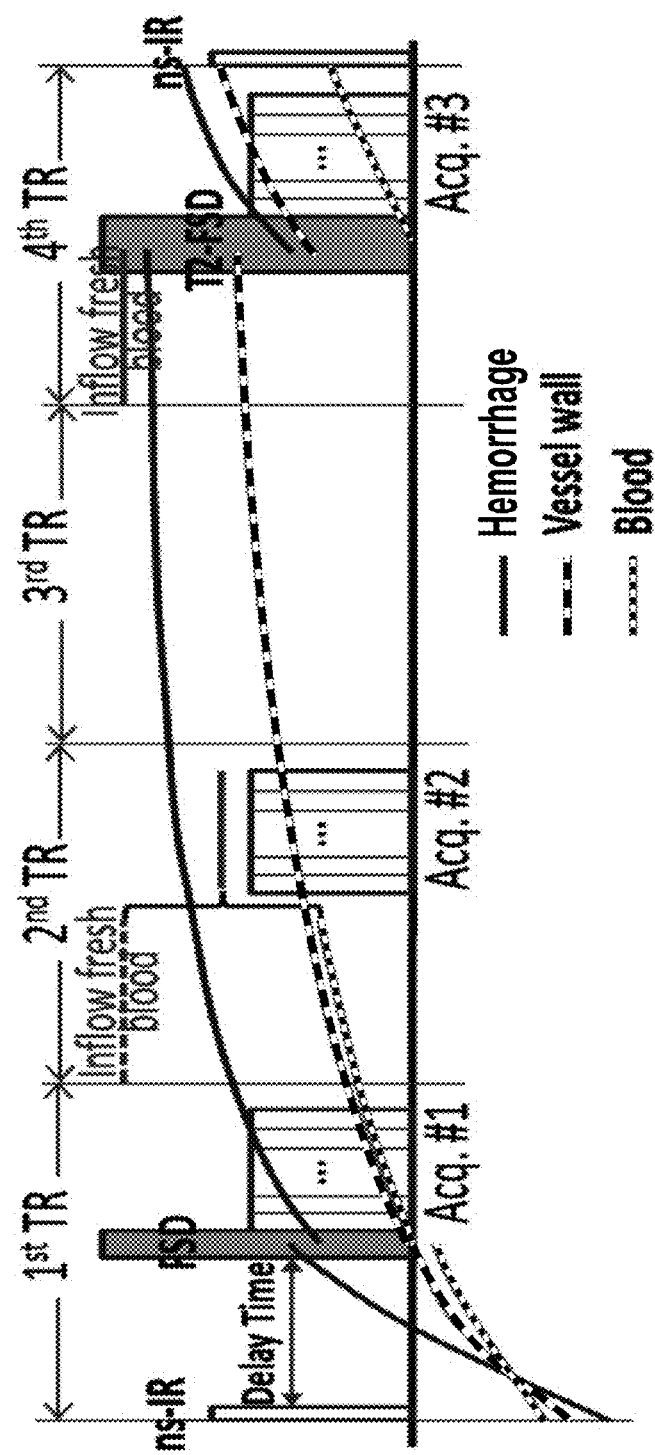
FIG. 1 demonstrates, in accordance with an embodiment of the invention, a schematic diagram of a Multicontrast Atherosclerosis Characterization (MATCH) sequence in which three contrast weightings are acquired in an interleaved fashion.

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., MRI in Practice $4^{th}$ ed.; and Guyton and Hall, Textbook of Medical Physiology $12^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions," "disease conditions," and "cardiovascular conditions," as used herein, may include but are in no way limited to atherosclerosis. Atherosclerotic lesions imaged according to the inventive methods described herein can include those found in the heart of a subject, as well as in other areas of the body.

"Mammal," as used herein, refers to any member of the class Mammalia, including, without limitation, humans and nonhuman primates such as chimpanzees and other apes and monkey species; farm animals, such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

By way of background, atherosclerosis is a chronic disease that can remain asymptomatic for decades. Atherosclerotic plaques can be separated into two broad categories: stable and unstable (also called vulnerable). The pathobiology of atherosclerotic lesions is complicated, but generally, stable atherosclerotic plaques, which are often asymptomatic, are rich in extracellular matrix and smooth muscle cells, while unstable plaques are rich in macrophages and foam cells and the extracellular matrix separating the lesion from the arterial lumen (also known as the fibrous cap) is usually weak and prone to rupture. The process of evaluating atherosclerosis in patients via MRI, in order to assess the nature and extent of any lesions present, is important to determining an appropriate treatment plan.

When imaging arterial plaque using MRI, spatial registration of multiple image sets is usually needed to correct for inter-scan misregistration artifacts and to ensure plaque characterization at the same location. This can be accomplished manually, or aided by computer software after scanning Unfortunately, the post-processing procedure is time-consuming and sometimes incomplete.

In order to solve this problem, the inventors developed a novel approach to MRI in which multiple spatially co-registered 3D image sets are acquired in an interleaved fashion and from the same volume within a subject. Using the inventive method, a single scan allows for comprehensive assessment of atherosclerotic plaque in a subject within a few minutes.

In various embodiments, the multiple image sets that are acquired provide multiple contrasts, including two or more of (1) black-blood hyper T1-weighting (T1-w), (2) grey-blood, and (3) black-blood T2-weighting (T2-w). In various embodiments of the invention, segmental sampling is periodically conducted following a non-selective inversion magnetization preparation. In some embodiments, imaging is accomplished according to a sequence that includes the steps of: (1) applying a non-selective inversion pulse to a volume of interest (VOI) in the subject; (2) applying a first flow-sensitive dephasing (FSD) preparation; (3) acquiring hyper T1-weighted data from the VOI in the subject; (4) acquiring grey-blood data from the VOI in the subject, subsequent to and dependent upon blood signal recovery and the inflow of fresh blood in a vessel within the VOI; (5) applying a second FSD preparation; and (6) acquiring T2-weighted data from the VOI at the end of the inversion recovery. In various embodiments, the duration of the first FSD preparation is shorter than that of the second FSD preparation. In some embodiments, the subject scanned is a mammal. In some embodiments, the subject scanned is a human.

In an embodiment, imaging parameters of the inventive method include: 60 segments per TR of 1200 ms, segment TR/TE=11.6/4.6 ms, flip angle=8°, in-plane resolution=0.55 mm, slice thickness=2 mm, 20 slices with 30% oversampling, water excitation, inversion time delay=470 ms, m1=935 mT·ms²/m, FSD/T2 duration=18/50 ms, centric reordering, parallel imaging GRAPPA (iPAT) factor=2, scan time=8 minutes.

In various embodiments, from 30 to 60 segments per TR can be used. In various embodiments, TRs ranging from 800 to 1400 ms can be used. In various embodiments, segment TR/TE can range from 9/3 to 12/5 ms. In various embodiments, the flip angle can range from 6 to 12 degrees. In various embodiments, in-plane resolution can range from 0.5 to 0.8 mm. In various embodiments, slice thickness can range from 0.5 to 3.0 mm. In various embodiments 4 to 40 slices are used with 20 to 50 percent oversampling. In various embodiments, inversion time delay is from 200 to 700 ms. In various embodiments, m1 is from 500 to 1500 mT·ms²/m. In various embodiments, FSD/T2 duration ranges from 16/25 to 30/50 ms. In various embodiments, iPAT ranges from 2 to 3. In various embodiments, scan time ranges from 4 to 8 minutes.

In some embodiments, MRI scanners that can be used in conjunction with the inventive can include, but are in no way limited to: 1.5, 3, and 7 Tesla whole-body systems. In some embodiments, the system used is made by a major vendor (e.g. GE, Philips, Siemens, or Toshiba). In some embodiments, a high-field small animal system (e.g. Bruker) is used. The data reported herein was collected on a 3-Tesla system (MAGNETOM Verio, Siemens Healthcare). In some embodiments, the MRI scanner used includes the components represented in FIG. 5.

Figure 5:
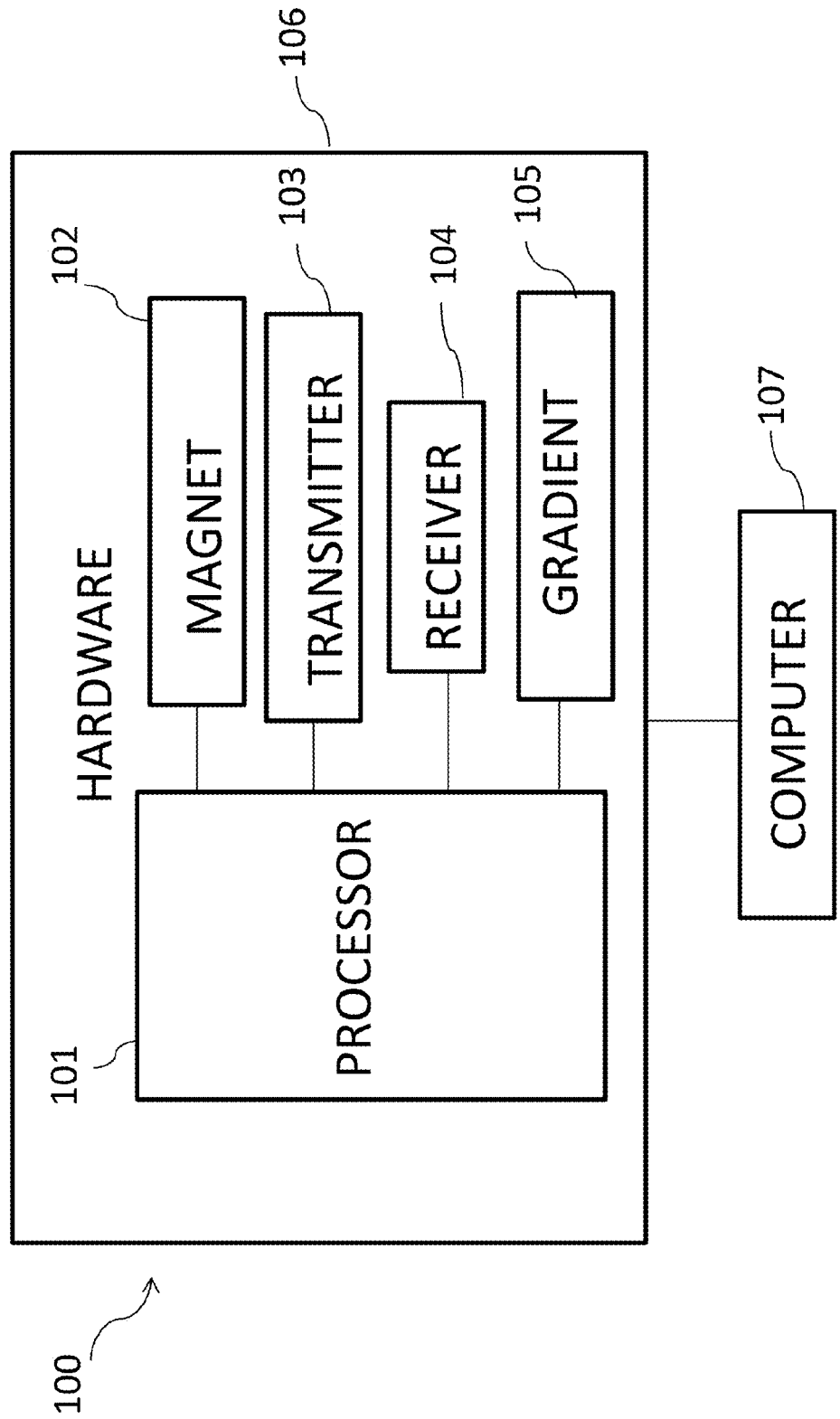
FIG. 5 depicts, in accordance with an embodiment of the invention, the central components of an MRI system.

In various embodiments, the invention teaches a method for characterizing one or more atherosclerotic lesions in a subject by (a) viewing images of the subject obtained by using an imaging system or method described herein; and (b) characterizing one or more atherosclerotic lesions in the subject on the basis of the presence or absence and/or extent of one or more characteristics demonstrated in the images that may include, but are in no way limited to: (i) intraplaque hemorrhage, (ii) calcified nodules, (iii) dense fibrous material, (iv) necrotic core, and (v) loose matrix. In various embodiments, the one or more atherosclerotic lesions are further characterized by determining whether any hemorrhage detected is relatively new or relatively old, based upon one or more of the images viewed. In some embodiments, the VOI can include, but is in no way limited to a region of the subject's heart. In various embodiments, the VOI includes an anatomical region that can include but is in no way limited to any of the following: an arterial wall, the brain, heart muscle, and parenchyma of an organ. In certain embodiments, the VOI can include one or more of the following structures: a coronary artery, an intracranial artery, a carotid artery, the aorta, a renal artery, and any arteries in the low extremities In some embodiments, the invention teaches a magnetic resonance imaging system that can include, but is in no way limited to: a magnet operable to provide a magnetic field; a transmitter operable to transmit a radio frequency pulse to a region within the magnetic field; a receiver operable to receive a magnetic resonance signal from the region; and a processor operable to control one or more of the magnet, transmitter and receiver; wherein the processor is configured to direct the transmitter and receiver to execute steps, including: (a) applying a non-selective inversion pulse to a volume of interest (VOI) in a subject; (b) applying a first flow-sensitive dephasing (FSD) preparation; (c) generating hyper T1-weighted magnetic resonance data from the VOI in the subject based upon the magnetic resonance signal; (d) generating grey-blood magnetic resonance data from the VOI in the subject based upon the magnetic resonance signal, subsequent to and dependent upon the blood signal recovery and inflow of fresh blood in a vessel within the VOI; (e) applying a second FSD preparation; and (f) generating T2-weighted data from the VOI based upon the magnetic resonance signal at the end of the inversion recovery. In some embodiments, the processor is configured to generate an image based on the magnetic resonance data. In certain embodiments, the duration of the first FSD preparation is shorter than that of the second FSD preparation. In some embodiments, the VOI can include, but is in no way limited to a region of the subject's heart. In certain embodiments, the VOI can include, but is in no way limited to one or more of the following: an arterial wall, the brain, heart muscle, and parenchyma of an organ. In certain embodiments, the VOI can include one or more of the following structures: a coronary artery, an intracranial artery, a carotid artery, the aorta, a renal artery, and any arteries in the low extremities In some embodiments, the invention teaches a non-transitory machine-readable medium having machine executable instructions for causing one or more processors of a magnetic resonance imaging machine to execute a method on the magnetic resonance imaging machine. In certain embodiments, the method includes: applying a non-selective inversion pulse to a volume of interest (VOI) in a subject; applying a first flow-sensitive dephasing (FSD) preparation; acquiring hyper T1-weighted magnetic resonance data from the VOI in the subject; acquiring grey-blood magnetic resonance data from the VOI in the subject, subsequent to and dependent upon blood signal recovery and the inflow of fresh blood in a vessel within the VOI; applying a second FSD preparation; acquiring T2-weighted magnetic resonance data from the VOI at the end of the inversion recovery; and generating an image based on the magnetic resonance data. In some embodiments, the duration of the first FSD preparation is shorter than that of the second FSD preparation. In some embodiments, the VOI can include, but is in no way limited to a region of the subject's heart. In various embodiments, the VOI includes an anatomical region that can include but is in no way limited to any of the following: an arterial wall, the brain, heart muscle, and parenchyma of an organ. In certain embodiments, the VOI can include one or more of the following structures: a coronary artery, an intracranial artery, a carotid artery, the aorta, a renal artery, and any arteries in the low extremities FIG. 5 depicts a view of system 100 according to one example. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103, in the figure, can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil.

Hardware 106 includes gradient 105. Gradient 105 can represent one or more coils used to apply a gradient for localization.

Processor 101, in communication with various elements of hardware 106, includes one or more processors configured to implement a set of instructions corresponding to a method as disclosed herein. For example, processor 101 can be configured to implement a set of instructions (stored in a memory of hardware 106) to deliver RF excitation and gradients and receive magnetic resonance data from a volume of interest.

Computer 107 is coupled to hardware 106. Computer 107 can include one or more of a desktop computer, a workstation, a server, or a laptop computer. In one example, computer 107 is user-operable and includes a display, a printer, a network interface or other hardware to enable an operator to control operation of the system 100.

One skilled in the art will recognize many methods and materials similar or equivalent to those described herein, which could be used in the practice of the present invention. Indeed, the present invention is in no way limited to the methods and materials described.

EXAMPLES

Example 1

Methods

The inventive "MATCH" (Multicontrast Atherosclerosis Characterization) sequence uses a low-flip-angle gradient echo-based MRI acquisition technique combined with specialized magnetization preparative schemes, and multiple co-registered 3D image sets with different contrast weightings are collected in an interleaved fashion.

As shown in FIG. 1, the interleaved acquisition of the inventive method consists of 4 repetition times (TRs). The first TR provides hyper T1-weighted (T1-w) contrast at the vessel wall by using a nonselective inversion pulse and a blood-suppressing FSD preparation. The second TR provides grey-to-bright blood lumen that is secondary to both blood T1-recovery and in-flow fresh blood. The third TR is for the vessel wall spins to continue to recover. Finally, the fourth TR provides T2-weighted (T2-w) contrast at the vessel wall by using a long-duration FSD preparation. The three contrasts are aimed to identify the intra-plaque hemorrhage, juxtaluminal calcification, and necrotic core, respectively.

The inventive technique was validated on 4 volunteers (all males) and 2 patients (males) with carotid plaques. Imaging parameters included: 60 segments per TR of 1200 ms, segment TR/TE=11.6/4.6 ms, flip angle=8°, in-plane resolution=0.55 mm, slice thickness=2 mm, 20 slices with 30% oversampling, water excitation, inversion time delay=470 ms, m1=935 mT·ms$^2$/m, FSD/T2 duration=18/50 ms, centric reordering, iPAT=2, scan time=8 minutes (depending on phase encoding sampling rate). For comparison, spatially matched T1-w and T2-w turbo spin echo (TSE) and TOF imaging were performed.

Example 2

Results & Discussion

Figure 2:
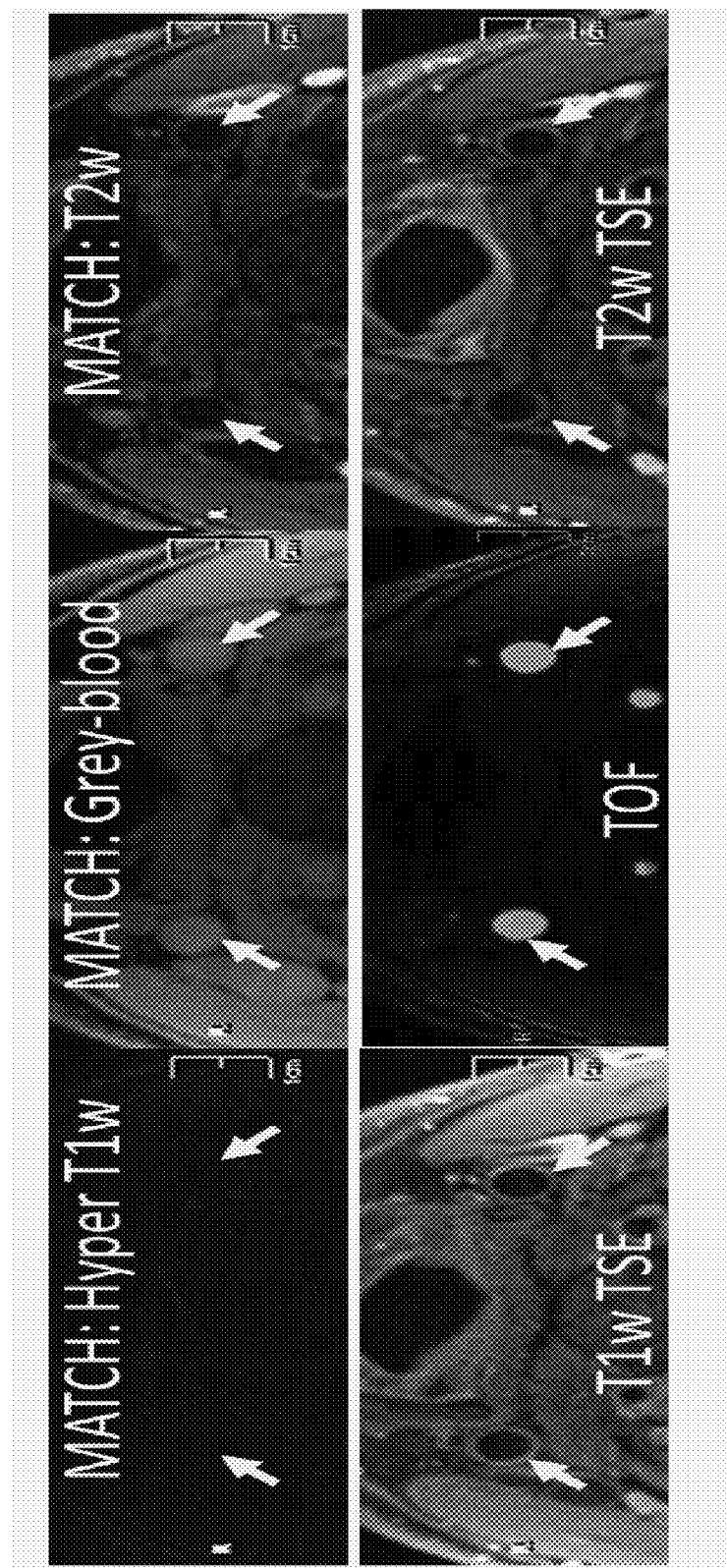
FIG. 2 demonstrates, in accordance with an embodiment of the invention, an image of a healthy 35 year old male volunteer. The vessel wall is well depicted.
Figure 3:
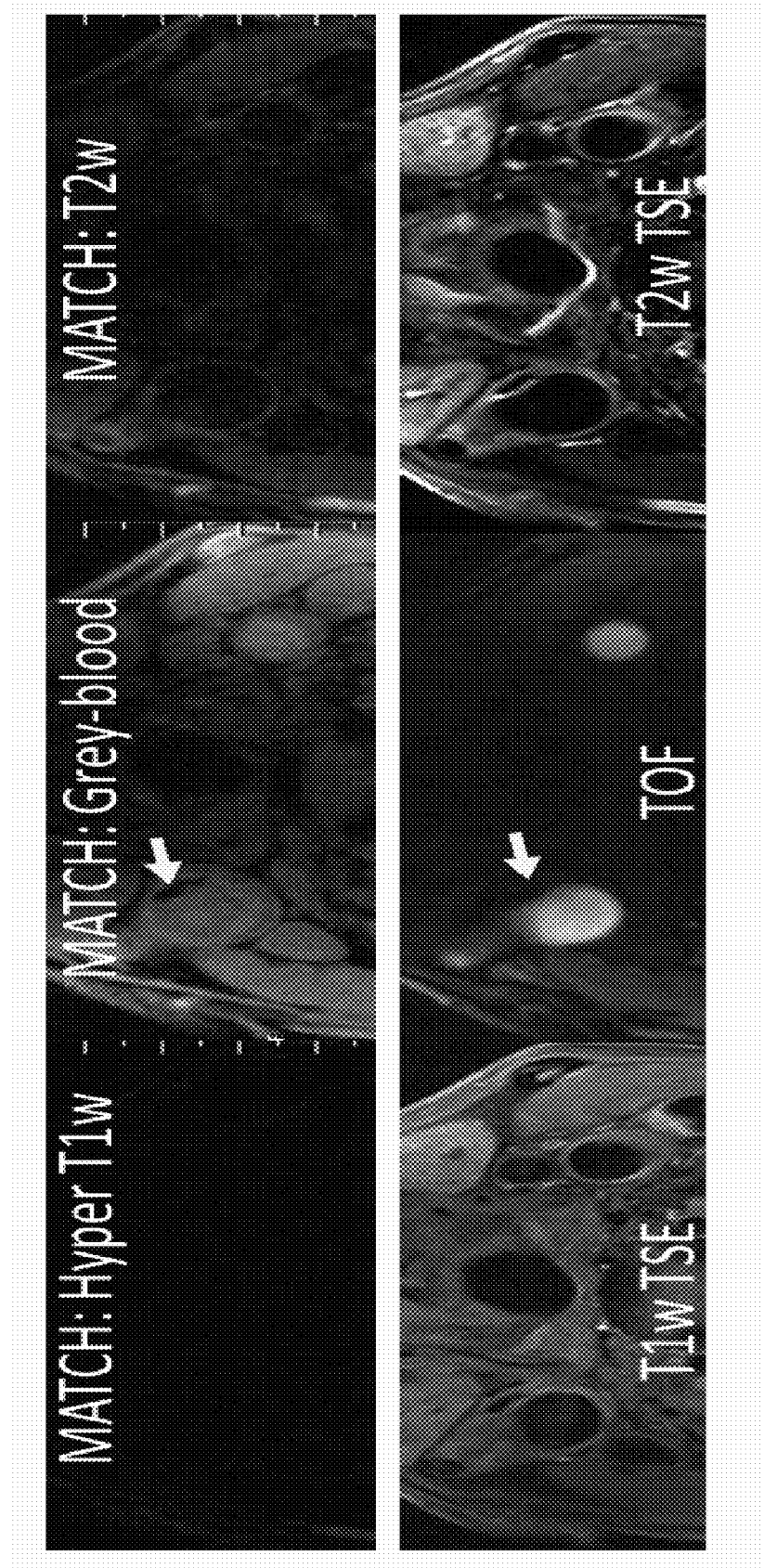
FIG. 3 demonstrates, in accordance with an embodiment of the invention, an image of a 72 year old male patient with juxtaluminal calcification, which is clearly identified on the grey-blood images, as confirmed by time-of-flight (TOF).
Figure 4:
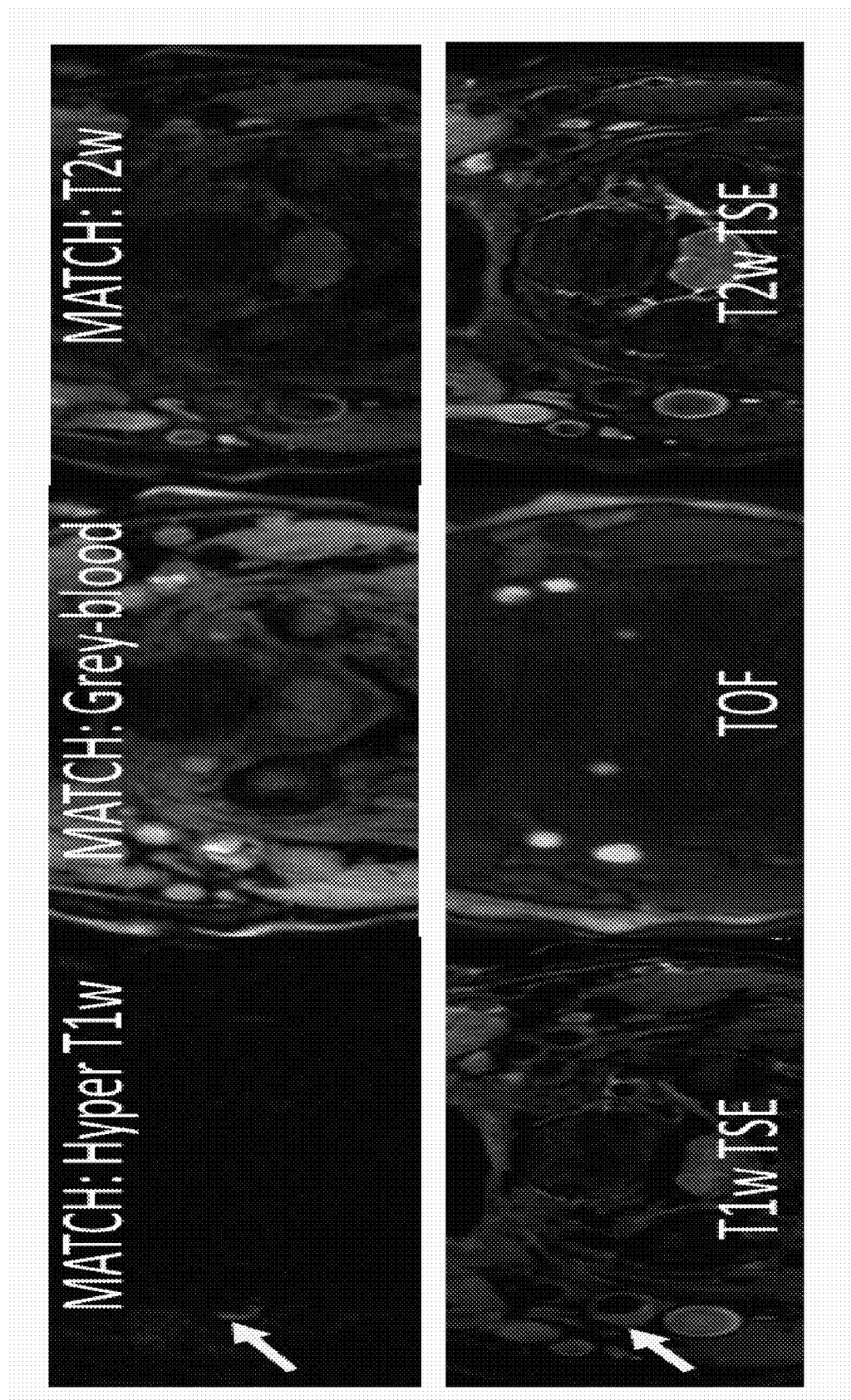
FIG. 4 demonstrates, in accordance with an embodiment of the invention, an image of a 72 year old male patient with intra-plaque hemorrhage, which is clearly identified on the hyper T1-weighted images, as confirmed by T1-weighted turbo spin echo (TSE).

With the optimized imaging parameters based on computer simulations, the "MATCH" technique described above was capable of providing nulled normal vessel wall on the first contrast weighting, iso-intense or brighter blood on the second contrast weighting, and dark-blood wall on the third contrast weighting, as observed in the healthy volunteer scans (FIG. 2). When applied to clinical cases, MATCH yielded focal signal voids for juxtaluminal calcification (FIG. 3) and hyper-intense depiction for hemorrhage (FIG. 4), both of which were confirmed by conventional protocol. The three 3D image sets that were obtained were spatially co-registered, markedly facilitating plaque assessment.

As demonstrated above, MATCH is a very useful technique for accurate plaque characterization. One of skill in the art would readily appreciate that mechanical improvements such as isotropic resolution and fast imaging would further improve the clinical value of the inventive techniques described herein.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for imaging an atherosclerotic lesion in a subject, comprising the steps of:
using an MRI machine to acquire multiple spatially co-registered 3D image sets in an interleaved fashion and from the same imaged volume of the subject, during a single scan, wherein the image sets are acquired by performing steps comprising:
(1) applying a non-selective inversion pulse to a volume of interest (VOI) in the subject;
(2) applying a first flow-sensitive dephasing (FSD) preparation;
(3) acquiring hyper T1-weighted data from the VOI in the subject;
(4) acquiring grey-blood data from the VOI in the subject, subsequent to and dependent upon blood signal recovery and the inflow of fresh blood in a vessel with the VOI;
(5) applying a second FSD and T2-weighted preparation; and
(6) acquiring T2-weighted data from the VOI, at the end of the scan.

2. The method of claim 1, wherein the duration of the first FSD preparation is shorter than that of the second FSD preparation.

3. The method of claim 1, wherein the subject is a mammal.

4. The method of claim 1, wherein the subject is a human.

5. The method of claim 1, wherein the VOI comprises a region of the subject's heart.

6. The method of claim 1, wherein the VOI comprises one or more anatomical structures selected from the group consisting of: an arterial wall, the brain, heart muscle, and parenchyma of an organ.

7. A method for characterizing one or more atherosclerotic lesions in a subject, comprising:
viewing images of the subject obtained by performing the method of claim 1; and
characterizing one or more atherosclerotic lesions in the subject on the basis of the presence or absence and/or extent of one or more characteristics demonstrated in the images and selected from the group consisting of (i) intra-plaque hemorrhage, (ii) calcified nodules, (iii) dense fibrous material, (iv) necrotic core, and (v) loose matrix.

8. The method of claim 7, wherein the one or more atherosclerotic lesions are further characterized by determining whether any hemorrhage detected is relatively new or relatively old, based upon one or more of the images viewed.

9. The method of claim 8, wherein any hemorrhage detected is characterized as relatively new or relatively old, based upon its signal appearance relative to other surrounding tissues on the T2-weighted image set.

10. A magnetic resonance imaging system, comprising:
a magnet operable to provide a magnetic field;
a transmitter operable to transmit to a region within the magnetic field;
a receiver operable to receive a magnetic resonance signal from the region; and
a processor operable to control the transmitter and the receiver; wherein the processor is configured to direct the transmitter and receiver to execute a sequence, comprising (a) applying a non-selective inversion pulse to a volume of interest (VOI) in a subject; (b) applying a first flow-sensitive dephasing (FSD) preparation; (c) acquiring hyper T1-weighted magnetic resonance data from the VOI in the subject; (d) acquiring grey-blood magnetic resonance data from the VOI in the subject, subsequent to and dependent upon blood signal recovery and the inflow of fresh blood in a vessel within the VOI; (e) applying a second FSD preparation; and (f) acquiring T2-weighted data from the VOI, at the end of the sequence; and wherein the processor is configured to generate an image based on the magnetic resonance data.

11. The system of claim 10, wherein the duration of the first FSD preparation is shorter than that of the second FSD preparation.

12. The system of claim 10, wherein the VOI comprises a region of the subject's heart.

13. The system of claim 12, wherein the VOI comprises one or more anatomical structures selected from the group consisting of: an arterial wall, the brain, heart muscle, and parenchyma of an organ.

14. A non-transitory machine-readable medium having machine executable instructions for causing one or more processors of a magnetic resonance imaging (MRI) machine to execute an MRI scan, comprising:
applying a non-selective inversion pulse to a volume of interest (VOI) in a subject;
applying a first flow-sensitive dephasing (FSD) preparation;
acquiring hyper T1-weighted magnetic resonance data from the VOI in the subject;
acquiring grey-blood magnetic resonance data from the VOI in the subject, subsequent to and dependent upon blood signal recovery and the inflow of fresh blood in a vessel within the VOI;
applying a second FSD preparation;
acquiring T2-weighted magnetic resonance data from the VOI, at the end of the scan; and
generating an image based on the magnetic resonance data.

15. The non-transitory machine-readable medium of claim 14, wherein the duration of the first FSD preparation is shorter than that of the second FSD preparation.

16. The non-transitory machine-readable medium of claim 14, wherein the VOI comprises a region of the subject's heart.

17. The non-transitory machine-readable medium of claim 14, wherein the VOI comprises one or more anatomical structures selected from the group consisting of: an arterial wall, the brain, heart muscle, and parenchyma of an organ.

* * * * *

UNITED STATES PATENT AND TRADEMARK OFFICE
CERTIFICATE OF CORRECTION

| | | |
|---|---|---|
| PATENT NO. | : 9,554,727 B2 | Page 1 of 1 |
| APPLICATION NO. | : 13/970327 | |
| DATED | : January 31, 2017 | |
| INVENTOR(S) | : Debiao Li et al. | |

It is certified that error appears in the above-identified patent and that said Letters Patent is hereby corrected as shown below:

In Column 1, at Line 4, insert the following after the TITLE before the FIELD OF THE INVENTION:

--STATEMENT REGARDING FEDERALLY SPONSORED RESEARCH OR DEVELOPMENT
This invention was made with government support under Grant No. HL096119 awarded by National Institutes of Health. The government has certain rights in the invention.--

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*